United States Patent [19]

Ciganek et al.

[11] Patent Number: 5,086,063
[45] Date of Patent: Feb. 4, 1992

[54] 4-ARYL-4-PIPERIDINE (OR PYRROLIDINE OR HEXAHYDROAZEPINE) CARBINOLS AND HETEROCYCLIC ANALOGS THEREOF

[75] Inventors: Engelbert Ciganek, Kennett Square, Pa.; Leonard Cook, Newark, Del.

[73] Assignee: Du Pont Merck Pharmaceutical Company, Wilmington, Del.

[21] Appl. No.: 398,996

[22] Filed: Aug. 28, 1989

Related U.S. Application Data

[62] Division of Ser. No. 174,356, Mar. 28, 1988, abandoned.

[51] Int. Cl.$^5$ ............... A61K 31/445; A61K 31/44; A61K 31/47
[52] U.S. Cl. ............... 514/326; 514/299; 514/311; 514/315; 514/317; 514/318; 514/319; 514/330; 514/331
[58] Field of Search ............... 514/315, 317, 330, 331, 514/299, 311, 318, 319, 326

[56] References Cited

U.S. PATENT DOCUMENTS

| | | | |
|---|---|---|---|
| 3,080,372 | 3/1963 | Janssen | 546/225 |
| 3,108,111 | 10/1963 | Stern et al. | 546/214 |
| 3,217,008 | 11/1965 | Kalm et al. | 546/223 |
| 4,072,686 | 2/1978 | Adelstein et al. | 546/194 |
| 4,194,045 | 3/1980 | Adelstein | 546/209 |
| 4,485,109 | 11/1984 | Ciganek | 514/317 |
| 4,783,471 | 11/1988 | Carr et al. | 514/317 |

FOREIGN PATENT DOCUMENTS

| | | |
|---|---|---|
| 36146 | 5/1973 | Australia. |
| 2158077 | 11/1971 | Fed. Rep. of Germany. |
| 47-18878 | 2/1971 | Japan. |
| 59106460 | 12/1982 | Japan. |

OTHER PUBLICATIONS

Iorio et al., *Tetrahedron*, 4983 (1971).
Bergel et al., *J. Chem. Soc.*, 26 (1944).
MacDonald et al., *Brit. J. Pharmacol.*, 1, 4 (1946).
Morrison et al., *J. Chem. Soc.*, 1467 (1950).
Kagi et al., *Helv. Chim. Acta.* 7, 2489 (1949).
Bondesson et al., *Drug Metab. Dispos.*, 9, 376 (1981).
Bondesson et al., *Acta Pharm. Suec.*, 17, 1 (1980).
Rogers et al., *J. Med. Chem.*, 1980, 23(6), 688-690, "Some Spiro Analogs of the Potent Analgesic Ketobemidone."

Primary Examiner—Frederick E. Waddell
Assistant Examiner—Kevin E. Weddington

[57] ABSTRACT

Known and novel 4-aryl-4-piperidinecarbinols and heterocyclic analogs are useful as analgesics. Also provided are novel pyrrolidinecarbinols and hexahydroazepine carbinols which are useful as analgesics, antidepressants and, in some cases, as anorectic agents.

16 Claims, No Drawings

4-ARYL-4-PIPERIDINE (OR PYRROLIDINE OR HEXAHYDROAZEPINE) CARBINOLS AND HETEROCYCLIC ANALOGS THEREOF

This is a division of application Ser. No. 07/174,356, filed Mar. 28, 1988, now abandoned.

FIELD OF THE INVENTION

This invention relates to pharmaceutical compositions for and methods of treating pain using 4-aryl-4-piperidinecarbinols and heterocyclic analogs thereof and to certain secondary pyridinecarbinols and heterocyclic analogs thereof which are novel compounds. This invention also relates to novel pyrrolidinecarbinols and hexahydroazepine carbinols which are useful for the treatment of pain. The novel compounds are also useful as antidepressants and, in some cases, as anoretic agents.

BACKGROUND INCLUDING PRIOR ART

The treatment of chronic moderate or severe pain is a difficult and sometimes unsuccessful medical challenge. Morphine and other opioid analgesics are often used to treat severe acute pain, but the development of tolerance, psychic and physical dependence, and potentially serious narcotic side effects limit their usefulness in treating chronic pain conditions. Antiinflammatory analgesics lack the strong analgesic efficacy of opioid analgesics and produce other serious side effects including gastrointestinal bleeding and gastric erosion that limits their usefulness in treating chronic severe pain.

Tricyclic antidepressant drugs are occasionally used as adjuncts in treating chronic pain associated with depressive disorders, but they lack the stronger analgesic potency of morphine-like drugs and produce potentially serious side effects of their own (A. G. Gilman, et al: Goodman and Gilman's The Pharmacological Basis of Therapeutics, Seventh Edition, Macmillan Publishing Co., New York, 1985). While tricyclic antidepressants are not recognized as primary analgesic agents, they are thought to modulate pain transmission via alterations in serotonin or norepinephrine uptake in the brain (S. Butler, Adv. Pain Res. Ther. 7:173-197, 1984).

Compounds of the invention show moderate-to-strong analgesic activity in mice, rats, and dogs. Unlike opioid analgesics, they lack activity at mu, kappa, delta, or sigma receptor sites in the brain. Studies in animals show that they lack the addictive and respiratory depressant properties of narcotic-related analgesics. Unlike antiinflammatory analgesics, they do not inhibit prostaglandin synthesase activity or show antiinflammatory effects in vivo. Like the tricyclic antidepressants, they inhibit uptake of serotonin, norepinephrine, and/or dopamine in rat brain preparations. However, analgesic doses of the compounds of the invention are not accompanied by anticholinergic side effects, sedation, or other signs of motor impairment observed with tricyclic antidepressants.

Many of the 4-arylpiperidinecarbinols of this invention, as shown below by Formula Ia, are known to have antidepressant activity. These compounds and methods for preparing them are disclosed in Ciganek, U.S. Pat. No. 4,485,109, issued Nov. 27, 1984, the disclosure of which is hereby incorporated by reference.

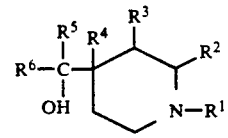

Ia wherein
(a) $R^1$ is H, alkyl of 1 to 12 carbon atoms, cycloalkyl of 3 to 8 carbon atoms or benzyl;
(b) each of $R^2$ and $R^3$ is independently selected from H and lower alkyl of 1 to 4 carbon atoms; $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;
(c) $R^4$ is
  (1) phenyl or 2-naphthyl or phenyl or 2-naphthyl substituted with one or two substituents, the same or different, selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;
  (2) 2-, 3-, or 4-biphenyl or 2-, 3- 4-biphenylyl wherein either or both aromatic moieties are substituted with one or two substituents, the same or different selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;
  (3) 2-pyrrolyl or 2-pyrrolyl substituted with one to three lower alkyl groups of 1 to 4 carbon atoms;
  (4) 2-, 3-, or 4-pyridyl; or
  (5) 2-thienyl substituted in the 5-position with lower alkyl of 1 to 4 carbon atoms;
(d) each of $R^5$ and $R^6$ is independently selected from alkyl of 1 to 12 carbon atoms and cycloalkyl of 3 to 8 carbon atoms or $R^5$ and $R^6$ taken together is a branched or unbranched alkylene bridge wherein the bridge is of 3 to 11 carbon atoms, provided, however, when $R^1$, $R^5$ and $R^6$ are methyl and $R^2$ and $R^3$ are H, then $R^4$ is not p-t-butylphenyl or 2'-biphenylyl. The invention herein also resides in esters of the aforesaid piperidinecarbinols with aliphatic mono- and dicarboxylic acids of 1 to 8 carbon atoms, in amine salts of the aforesaid piperidinecarbinols with pharmaceutically compatible inorganic acids, and in N-oxides of the aforesaid piperidinecarbinols.

In addition to the references cited in the specification of U.S. Pat. No. 4,485,109, the following references appear to be particularly pertinent.

U.S. Pat. No. 3,108,111 to Stern et al., Nov. 22, 1963, discloses piperidine compounds useful as cough suppressants and analgesics of the formula

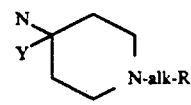

where

X is a phenyl group;
Y is a hydroxymethyl (CH₂OH), hydroxyethyl or hydroxypropyl group,
alk is an alkylene group (straight or branch-chain) containing up to six carbon atoms, and
R is:
- (a) an alkoxy group containing up to six carbon atoms, or
- (b) an aryloxy group, or
- (c) an aralkoxy group, or
- (d) a group containing a heterocyclic oxygen atom, or
- (e) an aryl group, or
- (f) a heterocyclic residue carrying a basic nitrogen atom (e.g., pyridine, piperdine, morpholine, piperazine), or
- (g) an alkoxy group carrying a further oxygenated substituent such as a hydroxy, ethoxy or phenoxy group.

U.S. Pat. No. 3,080,372 to Janssen, Mar. 5, 1963, discloses pharmaceutically useful compounds of the formula

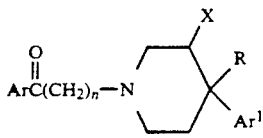

wherein
R is hydroxy (lower alkyl) amongst others;
X is H, or CH₃;
n=>2<5.

J5,9106-460-A discusses antifungal and analgesic compounds of the formula

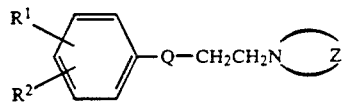

wherein
R¹ and R³=H, halogen, nitro or lower cycloalkyl;
Q is —CO—, —CH(OH)—, or —O—radical;

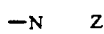

amongst others is

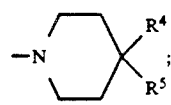

R⁴ is unsubstituted or halogenated phenyl, or pyridyl;
R⁵ is H, protected carboxyl, carbamoyl or hydroxy-lower alkyl.

BE 775,611 discloses 1-(3,3-diphenyl-1-propyl)-4-arylpiperidines as analgesics, spasmolytics and antitussive agents of the formula

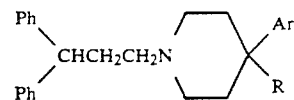

where
Ar is Ph;
R is CH₂OH amongst others;
R₁ is 1–4 C alkyl.

Several secondary piperidinecarbinols of the type described herein have been reported in the literature. Representative of these are M. A. Iorio et al., *Tetrahedron*, 4983 (1971); F. Bergel et al., *J. Chem. Soc.*, 26, (1944); A. D. MacDonald et al., *Brit J. Pharmacol.*, 1,4 (1946); A. L. Morrison et al., *J. Chem. Soc.*, 1467, (1950); H. Kagi et al., *Helv. Chim. Acta*, 7,2489 (1949); U. Bondesson et al., *Drug Metab. Dispos.*, 9,376 (1981); U. Bondesson et al., *Acta Pharm. Suec.*, 17, 1 1980). There is no analgesic activity in any of these references other than in A. L. Morrison et al., which discloses that 4-phenyl-1-methyl-4-(1-hydroxyethyl)piperidine and 4-phenyl-1-methyl-4-(1-hydroxypropyl)piperidine were much less active as analgesics than the parent ketones.

There is no indication in the known art that the compounds of this invention would be useful as analgesics and be devoid of the anticholinergic side effects, sedation, or other signs of motor impairment observed with tricyclic antidepressants.

SUMMARY OF THE INVENTION

It has been found that compounds of Formula (I) are useful as analgesics but lack the addictive and respiratory depressant properties of narcotic-related analgesics.

More particularly, according to the present invention, there is provided a method of treating pain which comprises administering an analgesic-effective amount of a compound of the formula:

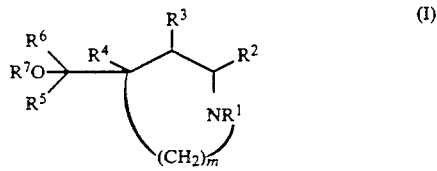
(I)

wherein
m is 1, 2 or 3;
R¹ is CH₃, C₂H₅, n—C₃H₇, or allyl;
R² and R³ independently are H or alkyl of 1–4 carbon atoms; or R¹ and R² taken together is a branched or unbranched alkylene bridge wherein the bridge is of 3 or 4 carbon atoms; or R² and R³ taken together is a branched or unbranched alkylene bridge wherein the bridge is of 3 to 6 carbon atoms;
R⁴ is:
- (a) phenyl or

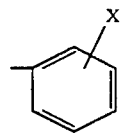

where X is one or two substituents, the same or different, selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl or 2-, 3-, or 4-biphenyl where either or both aromatic groups are substituted with 1 or 2 substituents, the same or different, selected from F, Cl, alkyl, perfluoroalkyl, alkoxy, aryloxy, alkylthio, perfluoroalkoxy, arylthio, perfluoroalkylthio and dialkylamino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CF_3$;

$R^5$ is alkyl of 1–4 carbon atoms, or is taken together with $R^6$ to form a branched or unbranched alkylene bridge of 3–11 carbon atoms;

$R^6$ is H, alkyl of 1–4 carbon atoms, or is taken together with $R^5$ to form a branched or unbranched alkylene bridge of 3–11 carbon atoms; and $R^7$ is H, alkyl of 1–4 carbon atoms, alkanoyl of 1–4 carbon atoms, or —$CH_2$ phenyl; or a pharmaceutically salt or N-oxide thereof, provided that when 1) $R^1$, $R^5$ and $R^6$ are methyl, and $R^2$ and $R^3$ are H, then $R^4$ is not $3,4\text{-}F_2C_6H_3$, $3,4\text{-}Cl_2C_6H_3$, p-t-butylphenyl, $2,3\text{-}(MeO)C_6H_3$, $2,5\text{-}(MeO)_2C_6H_3$, or 3-pyridyl;

2) $R^1$, $R^5$ and $R^6$ are methyl or $R^5$ and $R^6$ are taken together as —$(CH_2)_6$— and —$(CH_2)_7$, then $R^4$ is not $3\text{-}MeOC_6H_4$.

Also provided is a novel class of carbinols useful for the treatment of pain, having the formula:

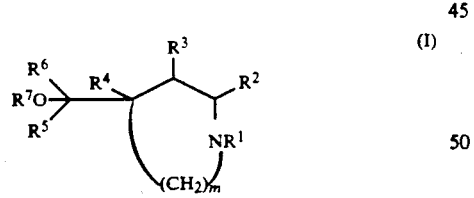

wherein (1) when m is 2 and $R^6$ is other than H, $R^1$, $R^2$ and $R^3$ are as defined above;

$R^4$ is (a)

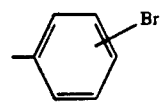

(b) 1-naphthyl optionally substituted with one or two substituents, the same or different, selected from F, Cl, Br; perfluoroalkyl, alkylthio, alkoxy, phenoxy, alkyl, alkyl- or dialkylamino, said alkyl in the alkyl-containing groups being 1–12 carbon atoms.

(c) 3-pyrrolyl optionally substituted with one to three alkyl groups of 1–4 carbon atoms, (d) 2-, or 3-thienyl optionally substituted with Cl, Br, or alkyl of 1–4 carbon atoms, provided when 2-thienyl is substituted with alkyl it is other than the 5-position, or (e) 2-, or 3-benzothienyl or benzofuryl optionally substituted on the aromatic ring with Cl, Br or $CF_3$;

$R^5$ independently is alkyl of 1–4 carbon atoms or when taken together with $R^6$ is a branched or unbranched alkylene bridge of 3–11 carbon atoms;

$R^6$ independently is alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —$CH_2$ phenyl; and (2) when m is 1 or 3, or when $R^6$ is H and m is 2; then $R^1$ independently is $CH_3$, $C_2H_5$, n—$C_3H_7$, or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms; or $R^2$ and $R^3$ taken together is a branched or unbranched alkylene bridge where the bridge is of 3 to 6 carbon atoms;

$R^4$ is:

(a) phenyl or

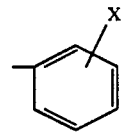

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CF_3$;

$R^5$ independently is alkyl of 1–4 carbon atoms, or when taken together with $R^6$ is a branched or unbranched alkylene bridge of 3–11 carbon atoms;

$R^6$ independently is H, alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —CH$_2$ phenyl; or a pharmaceutically suitable salt or N-oxide thereof, provided that when $R^6$ is H, $R^1$ is methyl and m is 2, then $R^4$ is other than $C_6H_5$, 2-MeOC$_6$H$_4$, 2,3-(MeO)$_2$C$_6$H$_3$ and pharmaceutically suitable salts or N-oxides thereof.

The novel compounds of this invention are also useful as antidepressants and as anorectic agents.

Preferred compounds are those of Formula (I) where when m is 2:

(a) $R^1$ is CH$_3$; or
(b) $R^2$ and $R^3$ are H; or
(c) $R^4$ is 2- or 3-thienyl, or

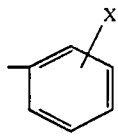

where X is Cl, Br, F, CF$_3$; or
(d) $R^5$ is CH$_3$; or
(e) $R^6$ is H or CH$_3$; or
(f) $R^7$ is H.

Preferred compounds are those of Formula (I) where when m is 1 or 3;

(a) $R^1$ is CH$_3$; or
(b) $R^2$, $R^3$ and $R^7$ are H; or
(c) $R^4$ is

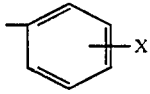

where X is Cl, Br, F or CF$_3$; or
(d) $R^5$ is CH$_3$; or
(e) $R^6$ is H or CH$_3$.

Specifically preferred for their analgesic activity are:

(a) 4-(3'-Chlorophenyl)-α,1-dimethylpiperidinemethanol (Example 1)
(b) 4-(3'-Chlorophenyl)-α,α,1-trimethyl-4-piperidinemethanol (Example 1a)
(c) 4-(3'-Bromophenyl)-α,1-dimethylpiperidinemethanol (Example 10)
(d) 4-(3'-Bromophenyl)-α,α,1-trimethyl-4-piperidinemethanol (Example 41)
(e) 4-(2-Thienyl)-α,1-dimethylpiperidinemethanol (Example 26)
(f) 4-(3-Thienyl)-α,1-dimethylpiperidinemethanol (Example 27)
(g) 4-(3'-Chlorophenyl)-α,1-dimethyl-2,3,4,5,6,7-hexahydro-1H-azepine-1-methanol (Example 57)
(h) 3-(3'-Chlorophenyl)-α,α,1-trimethyl-3-pyrrolidinemethanol (Example 56)

or pharmaceutically suitable salts thereof.

Specifically preferred for their antidepressant and anorexia activity are:

(a) 4(3'-Chlorophenyl)-α,1-dimethylpiperidinemethanol (Example 1)
(b) 4(4'-Trifluoromethylphenyl)-α-1-dimethylpiperidinemethanol (Example 16).

or a pharmaceutically suitable salt thereof.

METHOD OF PREPARATION AND PROCESS VARIABLES

The piperidinecarbinols (I, m = 2) can be prepared by the method described in U.S. Pat. No. 4,485,109, which is herein incorporated by reference, by using ketones $R^5COR^6$ to give tertiary carbinols or by using aldehydes $R^5CHO$ (not described in U.S. Pat. No. 4,485,109) to give secondary carbinols ($R^6$=H). This is the method of choice for tertiary carbinols where $R^5$ and $R^6$ taken together form a branched or unbranched chain of 3 to 11 carbon atoms. For most other carbinols, however, the preferred alternate method is as follows:

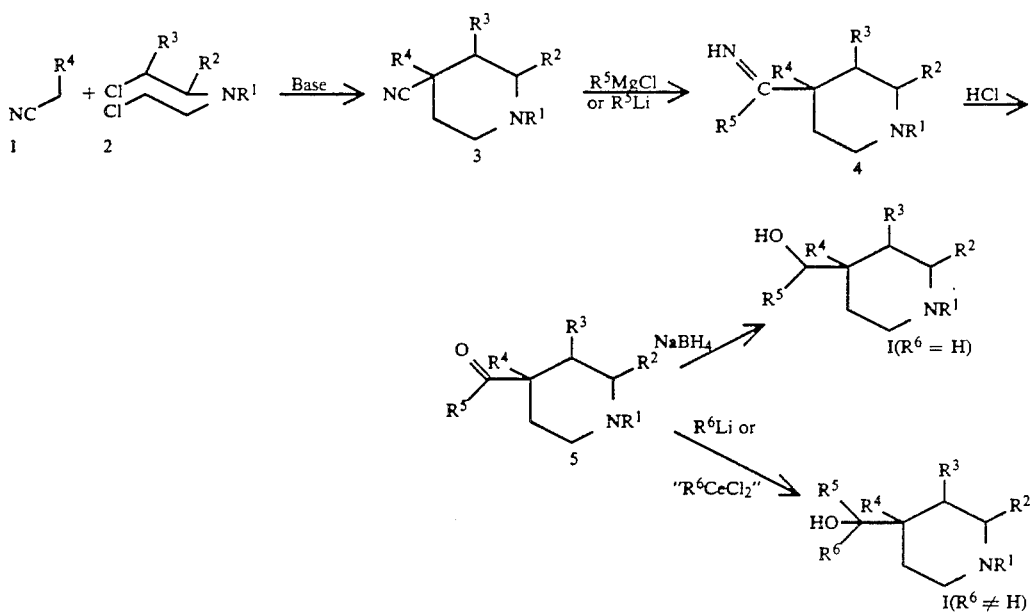

Reaction of a suitably substituted acetonitrile 1 with a bis-(2-chloroethyl) alkylamine 2 in the presence of a base by methods described in the literature gives a 4-piperidinecarbonitrile 3. The reaction can be carried out with sodium or potassium hydroxide in aqueous phase in the presence of a phase-transfer catalyst such as a quaternary ammonium or phosphonium salt; alternatively, bases such as sodium or potassium hydride, or sodium amide in an aprotic solvent such as dimethyl formamide, dimethyl sulfoxide, or tetrahydrofuran can be used. Temperatures are in the range of 25° to 150° C.

A piperidinecarbonitrile 3 is then reacted with an alkylmagnesium halide in an aromatic hydrocarbon solvent at a temperature in the range of 25°-150° C., or with an alkyllithium reagent in a mixture of ethyl ether and an aromatic or aliphatic hydrocarbon solvent at a temperature in the range of −50° to 100° C. Treatment with water gives the imine 4 which is then hydrolyzed with an aqueous inorganic acid, such as hydrochloric or sulfuric acid, to give the a ketone 5. Imine 4 carrying an $R^4$ group having substituents in the ortho portion usually need to be heated to 50°-100° C. to effect the hydrolysis; others hydrolyze at room temperature. The conversion of 3 to 5 via 4 is also a well-known method in the literature.

Reduction of a ketone 5 to a secondary alcohol (I, $R^6=H$) is best effected by sodium borohydride in ethanol or lithium borohydride in an ether solvent such as tetrahydrofuran at a temperature in the range of −20° to 50° C. Other hydride reducing agents, such as lithium aluminum hydride can also be used.

Treatment of a ketone 5 with alkyllithium reagents gives a tertiary cabinol (I, $R^6=$alkyl). More preferred reagents for carrying out the transformation are the alkyl cerium species obtained from anhydrous cerium chloride and alkyllithium reagents and described by T. Imamoto et al., *Tetrahedron Lett.*, 25, 4233(1984). These reagents give superior yields and fewer side reactions. For instance, for ketones 5 where $R^4$ contains groups that react with alkyllithium reagents (such as bromophenyl) only the cerium reagents give the desired products I in good yields. The reactions are carried out in ether solvents such as tetrahydrofuran at a temperature in the range of −100° to 50° C.

A tertiary carbinol of Formula I can also be prepared by reaction of the cerium species with an ester 6 which can be prepared from an nitrile 3 by methods described in the literature, such as hydrolysis with sulfuric acid followed by esterification.

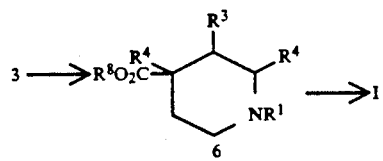

Pyrrolidinecarbinols (I, m=1) and hexahydroazepinecarbinols (I, m=3) are prepared analogously from the nitriles 7 or from the esters 8.

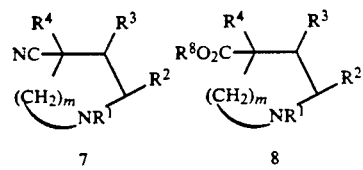

The latter are prepared by methods described in the literature.

Variation of $R^1$: compounds of Formula I with various groups $R^1$ can be prepared starting from the corresponding amines 2. Alternatively, a methyl group $R^1$ can be replaced by other groups as follows:

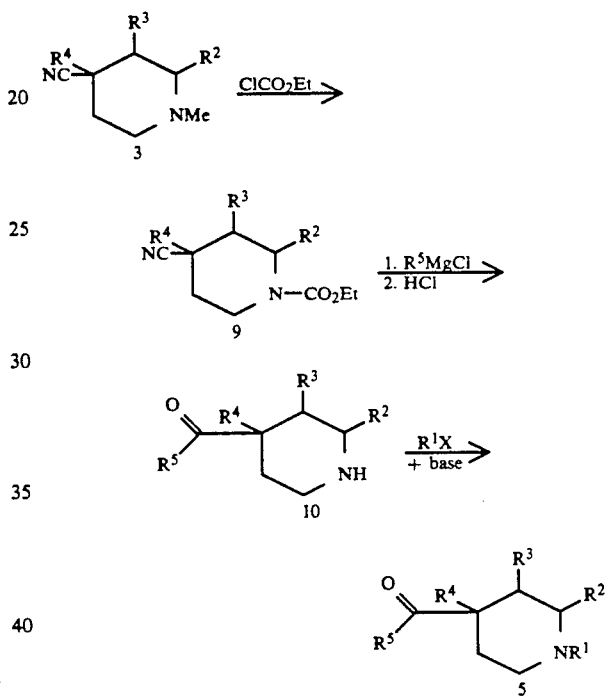

Nitriles 3, on heating with alkyl chloroformates in a hydrocarbon solvent such as benzene or toluene at a temperature in the range of 50°-150° C. give the urethanes 9. The latter, on reaction with a Grignard reagent in a hydrocarbon solvent such as benzene or toluene, give a ketones 10 where $R^1=H$. This ketone is converted into a ketones of Formula 5 with an alkyl or allyl halide $R^1X$ (X=Cl, Br or I) in a solvent such as dimethylformamide or tetrahydrofuran, at a temperature in the range of 0°-100° C. in the presence of a base such as sodium or potassium carbonate.

A ketone of Formula 10 can also be obtained by treating a ketone 5 ($R^1=$Me) with alkyl chloroformates as described above to give a urethane of Formula 11. This compound, on hydrolysis with an aqueous acid, such as hydrochloric or sulfuric acid, at a temperature of 50°-100° C., gives a ketone of Formula 10.

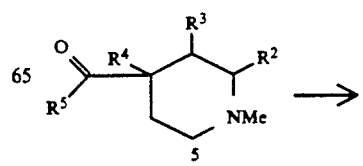

11

-continued

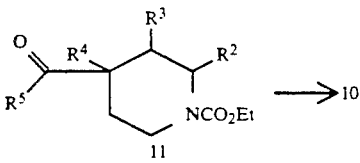

For secondary carbinols (I, $R^6$=H) having groups $R^1$=CH$_2$R$^9$ the following methods can also be used.

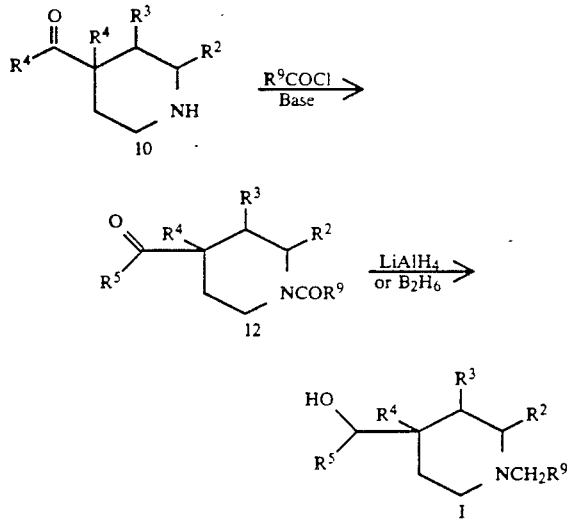

$R^9$ is either methyl or ethyl which on reduction of 12 gives compounds of Formula I where $R^1$ is ethyl or n-propyl respectively.

Ketones 10, on treatment with an acyl chloride $R^9$COCl in the presence of a base, such as sodium or potassium hydroxide in aqueous solution, or pyridine in an aprotic solvent such as methylene chloride, at temperatures of −30° to 50°, give the amides 12 which on reduction with borane or complex hydrides such as lithium aluminum hydride give the secondary carbinols I. This method is exemplified by Example 2.

Esters of compounds I ($R^7$=alkanoyl) are prepared by treatment of compounds I ($R^7$=H) with a suitable anhydride, or an acid chloride in the presence of a base such as pyridine, at temperatures of 0°-150°.

Ethers of compounds I ($R^7$=alkyl or CH$_2$Ph) are prepared by treatment of compounds I ($R^7$=H) with a base, such as sodium or potassium hydride, or sodium amide, in an aprotic solvent such as tetrahydrofuran or dimethylformamide at a temperature in the range of 0°-100° C., followed by addition of a halide $R^7$X (X=Cl, Br or I) at temperatures of 0°-100° C. Any quaternary ammonium salts of I formed are then converted into the tertiary bases I by treatment with potassium methylmercaptide in an aprotic solvent such as dimethylformamide at a temperature in the range of 50°-150° C. Alternatively, such ethers can be prepared by reaction of compounds I ($R^7$=H) with diazoalkanes $R^{11}$CHN$_2$ ($R^{11}$=H, alkyl or phenyl) in the presence of a catalyst such as a rhodium complex.

Suitable salts formed with pharmacologically acceptable acids, such as hydrochloric, sulfuric, phosphoric and maleic acids, can also prepared. Such salts are usually preferable when the free bases are oils. Such salts may also be more stable to storage, and may be better absorbed orally, than the free bases.

In the following examples, all temperatures are in degrees Celsius and parts and percentages are by weight. In the tables, "Me" is CH$_3$, "Et" is ethyl, "Pr" is propyl, "Ph" is phenyl and "Ac" is acetyl.

EXAMPLE 1

4-(3'-Chlorophenyl)-α,1-dimethyl-4-piperidinemethanol(I, m=2; $R^1$,$R^5$=Me; $R^2$,$R^3$,$R^6$,$R^7$=H; $R^4$=3-ClC$_6$H$_4$)

Sodium borohydride (3.5 g, 92 mmoles) was added slowly to a cooled mixture of 23.9 g (95 mmoles) of 1-[4-(3'-chlorophenyl)-1-methyl-4-piperidinyl]ethanone and 100 mL of ethanol. Water was added after stirring at room temperature for 2 hours, and the mixture was extracted with methylene chloride to give 24.1 g of crude product. A sample crystallized from ethyl acetate had m.p. 125°-126°, NMR(CDCl$_3$): δ7.2-7.4 (m,4H); 3.6 (quartet, J=7 Hz,1H); 2.8 (m,2H); 1.5-2.5 (m,10H) and 1.0 (d, J=7 Hz,3H).

The hydrochloride had m.p. 202°-205° after crystallization from isopropyl alcohol. Anal. Calcd. for C$_{14}$H$_{21}$Cl$_2$NO: C, 57.93; H, 7.29; N, 4.83. Found: C, 57.92; H, 7.14; N, 5.11.

The starting material, 1-[4-(3'-chlorophenyl)-1-methyl-4-piperidinyl]ethanone was obtained by either of the two following methods:

(a) To 400 mL of toluene was added 117 mL (0.35 mole) of 3M methylmagnesium chloride in tetrahydrofuran. Using a Vigreux column, 300 mL of solvent were then distilled off during 1 hour. To the cooled residue was added 47 g (0.20 mole) of 4-(3'-chlorophenyl)-1-methylpiperidine-4-carbonitrile, and the mixture was heated under reflux for 2 hours. Ten percent hydrochloric acid (400 mL) was added to the mixture, keeping the temperature below 25°. The layers were separated after stirring at room temperature for 6 hours, and the toluene was extracted with 50 mL of water. The combined water layers were made strongly basic with conc. ammonium hydroxide solution. Extraction with methylene chloride, removal of the solvent from the dried extracts, and rapid short-path distillation of the residue (160° bath temperature, 0.1 mm) gave 44.2 g (88% yield) of 1-[4-(3'-chlorophenyl)-1-methyl-4-piperidinyl]ethanone as an oil that rapidly crystallizes. NMR (CDCl$_3$): δ7.2-7.4 (m,4H); 2.7 (m,2H); 2.5 (m,2H); 2.3 (s,3H); 2.0-2.3 (m,4H) and 2.0 (s,3H). IR (neat) 1708 cm$^{-1}$.

(b) To 12.37 g (52 mmoles) of 4-(3-chlorophenyl)-1-methylpiperidine-4-carbonitrile dissolved in 75 mL of toluene was added 75 mL of 1.4M methyl lithium in ether (105 mmoles), keeping the temperature below 0°. The mixture was stirred at 0° for 30 minutes and at 25° for 3 hours. Ten percent hydrochloric acid (100 mL) was added and the mixture was stirred at room temperature for 3 hours. The layers were separated, and the toluene/ether layer was extracted with 20 mL of water. The combined aqueous phases were made strongly basic with aqueous sodium hydroxide and the mixture was extracted with methylene chloride. Removal of the solvent from the dried solution gave 12.7 g of crude 1-[4-(3'-chlorophenyl)-1-methyl-4-piperidinyl]ethanone, identical by NMR and IR spectroscopy with the product prepared according to procedure (a).

The starting material, 4-(3-chlorophenyl)-1-methylpiperidine-4-carbonitrile was prepared as follows by the procedure of T. Cammack and P. C. Reeves, J. Hetero-

*cycl. Chem.*, 23, 73 (1986): a mixture of 100 g (0.52 mole) of N,N-bis(chloroethyl)methylamine hydrochloride, 80 g (0.53 mole) of 3-chlorobenzyl cyanide, 13 g of hexadecyltributylphosphonium bromide and 750 mL of 50% aqueous sodium hydroxide was stirred at 100° internal temperature for 1 hour. Water (750 mL) was added to the cooled mixture which was then extracted with 500 mL and three 100-mL portions of toluene. Removal of the solvent from the dried solution and rapid short-path distillation of the residue (160° bath temperature, 0.1 mm) gave 107.2 g (88% yield) of 4-(3-chlorophenyl)-1-methylpiperidine-4-carbonitrile as a colorless oil which slowly crystallizes. NMR (CDCl$_3$): δ7.5 (s,1H); 2.3 (m,3H); 3.0 (d,2H); 2.5 (m,2H); 2.4 (s,3H) and 2.1 (m,4H). The hydrochloride had m.p. 235°–236° after crystallization from isopropyl alcohol.

EXAMPLE 1A 4-(3'-Chlorophenyl)-α,α,1-trimethyl-4-piperidinemethanol (I, m=2; $R^1$,$R^5$; $R^6$=Me; $R^2$,$R^3$,$R^7$=H; $R^4$=3-ClC$_6$H$_4$)

This compound was made by a modification of the general method described by T. Imamoto, Y. Sagiura, and N. Takiyama, *Tetrahedron Lett.*, 25, 4233 (1984) for the addition of organocerium reagents to ketones: cerium chloride heptahydrate (3.39 g, 9.1 mmoles) was dried at 140°/0.1 mm for 2 hours. Tetrahydrofuran (20 mL) was added with ice cooling, and the mixture was stirred under nitrogen for 2 hours. Methyl lithium (6.5 mL of an 1.4M solution in ether, 9.1 mmoles) was added at −70°, and the mixture was stirred at −70° for 30 minutes. A solution of 0.72 g (2.7 mmoles) of 1-[4-(3'-chlorophenyl)-1-methyl-4-piperidinyl]ethanone (Example 1) in 2 mL of tetrahydrofuran was added at −70°, and the mixture was allowed to come to room temperature. Methylene chloride and aqueous ammonium hydroxide solution were added, keeping the temperature below 0°. The mixture was filtered, and the solids were washed repeatedly with methylene chloride. The layers in the combined filtrate were separated and the methylene chloride layer was dried. Removal of the solvent gave 0.76 g of the title compound, identical by NMR and IR spectroscopy with the product obtained by the procedure described in U.S. Pat. No. 4,485,109. The hydrochloride had m.p. 276° (dec.) after crystallization from ethanol. Anal. Calcd. for C$_{15}$H$_{23}$Cl$_2$NO: C, 59.21; H, 7.62; N, 4.60. Found: C, 59.08; H, 7.70; N, 4.37.

4-(3'-Chlorophenyl)-α,α,1-trimethyl-4-piperidinemethanol was also prepared using the above procedure but starting with ethyl 4-(3-chlorophenyl)-1-methylpiperidine-4-carboxylate. The latter was prepared as follows by the procedure of J. Diamond, W. F. Bruce, and F. T. Tyson, *J. Org. Chem.*, 22, 399 (1957): 4-(3-chlorophenyl)-1-methylpiperidine-4-carbonitrile (Example 1) was added to 15 mL of 80% of sulfuric acid and the mixture was stirred in an 125° oil bath for 4 hours. Ethanol (60 mL) was added with cooling, and the mixture was heated under reflux for 16 hours and then poured onto ice. The aqueous mixture was extracted with methylene chloride and the extracts were washed with aqueous sodium carbonate. Removal of the solvent from the dried methylene chloride solution and short-path distillation of the residue (180° bath, 1 micron) gave 9.23 g (67%) of ethyl 4-(3-chlorophenyl)-1-methylpiperidinecarboxylate. NMR (CDCl$_3$): δ7.4 (s,1H); 7.3 (m,3H); 4.1 (quartet, J=7 Hz,2H); 2.8 (d,2H); 2.6 (d,2H); 2.3 (s,3H); 2.2 (t,2H); 2.0 (t,2H) and 1.2 (t,J=7 Hz,3H).

EXAMPLE 2

4-(3'-Chlorophenyl)-1-ethyl-α-methyl-4-piperidinemethanol (I, m=2; $R^1$=Et; $R^4$=3-ClC$_6$H$_4$; $R^5$=Me; $R^2$,$R^3$,$R^6$,$R^7$=H)

Ethyl chloroformate (6.5 g) was added to a solution of 5.0 g of 1-[4-(3'-chlorophenyl)-1-methyl-4-piperidinyl]-ethanone (Example 1) in 25 mL of benzene. The mixture was heated under reflux for 3 hours, cooled, and filtered. The filtrate was washed with 10% aqueous sodium carbonate, dried and concentrated to give 5.71 g of ethyl 4-acetyl-4-(3'-chlorophenyl)-1-piperidine carboxylate (11; $R^2$,$R^3$=H; $R^4$=3-ClC$_6$H$_4$).

A mixture of 4.69 g of the above product, 25 mL of conc. hydrochloric acid, and 10 mL of water was heated under reflux for 18 hours. The cooled mixture was made basic with 15% aqueous sodium hydroxide solution and extracted with methylene chloride to give 3.35 g of 1-[4-(3'-chlorophenyl)-4-piperidinyl]ethanone (10, $R^1$,$R^2$,$R^3$=H; $R^4$=3-ClC$_6$H$_4$). The hydrochloride had m.p. 254° (dec.). Anal. Calcd. for C$_{13}$H$_{17}$Cl$_2$NO; C, 56.94; H, 6.25; N, 5.11. Found: C, 56.89; H, 6.38; N, 5.51.

To a mixture of 1.0 g of the above free base, 10 mL of methylene chloride and 20 mL of 15% aqueous sodium hydroxide was added with cooling 1 mL of acetyl chloride and the mixture was stirred at room temperature for 1 hour. The aqueous phase was extracted with methylene chloride, and the combined organic phases were dried and concentrated to give 1.15 g of 1,4-diacetyl-4-(3'-chlorophenyl)-1-piperidine (12, $R^2$,$R^3$=H; $R^4$=3-ClC$_6$H$_4$; $R^5$,$R^9$=Me).

The above amide was dissolved in 10 mL of dry tetrahydrofuran, and 1 mL of borane methyl sulfide complex was added. The mixture was heated under reflux for 6 hours, cooled, and treated with 5 mL of conc. hydrochloric acid. The solvents were removed under vacuum, and the residue was heated with 20 mL of 10% hydrochloric acid in an 100° oil bath for 2 hours. The cooled mixture was made basic with aqueous sodium hydroxide and extracted with methylene chloride to give 0.90 g of the crude title compound. It was purified by short-path distillation (to 200° bath temperature, 1 micron) followed by crystallization from ethyl acetate. M.p. 89°–94°; NMR (CDCl$_3$): δ7.2–7.4 (m,4H); 3.7 (quartet, J=7 Hz,1H); 2.8 (d,2H); 1.2–2.5 (m,9H); 1.0 (t,J=7 Hz,3H) and 0.9 (d,J=7 Hz,3H). Anal. Calcd. for C$_{15}$H$_{22}$ClNO: C, 67.27; H, 8.28; N, 5.23. Found: C, 67.18; H, 8.14; N, 5.21.

Table 1 is illustrative of the novel aryl piperidinecarbinols which were prepared or could be prepared by the methods listed hereinabove but is not meant to be limiting in breadth.

TABLE 1

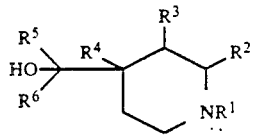

| Ex. No. | $R^1$ | $R^2$ | $R^3$ | $R^4$ | $R^5$ | $R^6$ | Mp °C. |
|---|---|---|---|---|---|---|---|
| 1 | Me | H | H | 3-ClC$_6$H$_4$ | Me | H | 202–205* |
| 1a | Me | H | H | 3-ClC$_6$H$_4$ | Me | Me | 278 (dec)* |
| 2 | Et | H | H | 3-ClC$_6$H$_4$ | Me | H | 89–94 |
| 3 | Me | H | H | C$_6$H$_5$ | Me | H | 119–120 |
| 4 | Me | H | H | 2-FC$_6$H$_4$ | Me | H | 181–184 (dec)** |
| 5 | Me | H | H | 3-FC$_6$H$_4$ | Me | H | 127–128 |
| 6 | Me | H | H | 4-FC$_6$H$_4$ | Me | H | 142–143 |
| 7 | Me | H | H | 3,4-F$_2$C$_6$H$_3$ | Me | H | 135–136 |
| 8 | Me | H | H | 4-ClC$_6$H$_4$ | Me | H | 171–172 |
| 9 | Me | H | H | 3,4-Cl$_2$C$_6$H$_3$ | Me | H | 175–177 |
| 10 | Me | H | H | 3-BrC$_6$H$_4$ | Me | H | 179 (dec)** |
| 11 | Me | H | H | 4-BrC$_6$H$_4$ | Me | H | 186 |
| 12 | Me | H | H | 2-MeC$_6$H$_4$ | Me | H | 102–106 |
| 13 | Me | H | H | 3-MeC$_6$H$_4$ | Me | H | 97–99 |
| 14 | Me | H | H | 4-MeC$_6$H$_4$ | Me | H | 161–163 (dec)** |
| 15 | Me | H | H | 3-CF$_3$C$_6$H$_4$ | Me | H | 111–112 |
| 16 | Me | H | H | 4-CF$_3$C$_6$H$_4$ | Me | H | 188–189 |
| 17 | Me | H | H | 4-MeOC$_6$H$_4$ | Me | H | 114–115 |
| 18 | Me | H | H | 3-Me$_2$NC$_6$H$_4$ | Me | H | |
| 19 | Me | H | H | 3-MeSC$_6$H$_4$ | Me | H | |
| 20 | Me | H | H | 3,5-Cl$_2$C$_6$H$_3$ | Me | H | |
| 21 | Me | H | H | 3-CF$_3$C$_6$H$_4$ | Me | H | |
| 22 | Me | H | H | 3-C$_6$H$_5$OC$_6$H$_4$ | Me | H | |
| 23 | Me | H | H | 3-C$_6$H$_{13}$C$_6$H$_4$ | Me | H | |
| 24 | Me | H | H | 2-C$_3$H$_7$SC$_6$H$_4$ | Me | H | |
| 25 | Me | H | H | 2-naphthyl | Me | H | 191–192 |
| 26 | Me | H | H | 2-thienyl | Me | H | 104–105 |
| 27 | Me | H | H | 3-thienyl | Me | H | 126–127 |
| 28 | Me | H | H | 2-benzothienyl | Me | H | |
| 29 | Me | H | H | 3-benzothienyl | Me | H | 184–188 (dec)** |
| 30 | Me | H | H | 2-benzofuryl | Me | H | |
| 31 | Me | H | H | 3-benzofuryl | Me | H | |
| 32 | Me | H | H | 2-pyridyl | Me | H | |
| 33 | Me | H | H | 3-pyrrolyl | Me | H | |
| 34 | n-Pr | H | H | 3-ClC$_6$H$_7$ | Me | H | 108–110 |
| 35 | Me | H | H | 3-ClC$_6$H$_4$ | Et | H | 123.5–125 |
| 36 | Me | H | H | 3-ClC$_6$H$_4$ | n-Pr | H | 150–153** |
| 37 | Me | H | H | 3-ClC$_6$H$_4$ | n-Bu | H | 95–96 |
| 38 | allyl | Me | H | 3-Cl$_6$H$_4$ | Me | H | |
| 39 | Me | —(CH$_2$)$_4$— | | 3-ClC$_6$H$_4$ | Et | H | |
| 40 | Et | H | Me | 3-ClC$_6$H$_4$ | n-Bu | H | |
| 41 | Me | H | H | 3-BrC$_6$H$_4$ | Me | Me | 285 (dec)* |
| 42 | allyl | H | H | 3-ClC$_6$H$_4$ | Me | Me | 131–132** |
| 43 | Me | H | H | 2-thienyl | Me | Me | 133–134 |
| 44 | Me | H | H | 3-thienyl | Me | Me | 157–158 |
| 45 | Me | H | H | 3-benzothienyl | Me | Me | 134–135 |
| 46 | Me | H | H | 2-pyridyl | Me | Me | 91–92 |
| 47 | Me | H | H | 2-benzothienyl | Me | Me | |
| 48 | Me | H | H | 3-benzofuryl | Me | Me | |
| 49 | Me | H | H | 3-(1'-methylpyrrolyl) | Me | Me | |
| 50 | Me | H | H | 1-naphthyl | Me | Me | 131–132 |
| 51 | Me | H | H | 3-(5'-chlorothienyl) | Me | Me | |
| 52 | Me | n-Bu | m-Pr | 3-ClC$_6$H$_4$ | Me | H | |
| 53 | —(CH$_2$)$_3$— | | H | 3-ClC$_6$H$_4$ | Me | H | |
| 54 | Me | —(CH$_2$)$_6$— | | 3-ClC$_6$H$_4$ | Me | H | |
| 55 | Me | H | H | 3-(n-C$_{10}$H$_{22}$)C$_6$H$_4$ | Me | H | |
| 56 | Me | H | H | 3-C$_6$H$_5$-5-ClC$_6$H$_3$ | Me | H | |
| 57 | Me | H | H | 3-C$_6$H$_5$C$_6$H$_3$Cl-5 | Me | H | |
| 58 | Me | H | H | 3-(3'-ClC$_6$H$_4$)C$_6$H$_4$ | Me | H | |
| 59 | Me | H | H | 3-Cl-1-naphthyl | Me | H | |
| 60 | Me | H | H | 2-(3-CH$_3$-thienyl) | Me | H | |
| 61 | Me | H | H | 2-(5-Cl-benzothienyl) | Me | H | |
| 62 | Me | H | H | 2-(5-Cl-benzofuryl) | Me | H | |
| 63 | Me | H | H | 3-(5-Cl-benzofuryl) | Me | H | |
| 64 | Me | H | H | 3-BrC$_6$H$_4$ | —(CH$_2$)$_3$— | | |
| 65 | Me | H | H | 3-BrC$_6$H$_4$ | —(CH$_2$)$_6$— | | |

*Hydrochloride salt
**Fumarate salt

EXAMPLE 66

4-(3'-Chlorophenyl)-α,1-dimethyl-4-piperidinemethanol Acetate (I; m=2; $R^1, R^5$=Me; $R^4$=3-ClC$_6$H$_4$; $R^2, R^3, R^6$=H; $R^7$=CH$_3$CO)

A mixture of 1.00 g of 4-(3'-chlorophenyl)-α,1-dimethyl-4-piperidinemethanol (Example 1) and 5 mL of acetic anhydride was heated under reflux for 90 minutes. Removal of the excess acetic anhydride and short-path distillation of the residue (170° bath temperature, 1 micron) gave 1.05 g of the title compound as an oil. NMR (CDCl$_3$): δ7.1-7.4 (m,4H); 4.9 (quartet, J=7 Hz,1H); 2.8 (m,2H); 2.2 (s,3H); 2.0 (s,3H); 1.9-2.4 (m,6H); and 0.9 (d,J=7 Hz,3H).

The salt with fumaric acid had m.p. 194° (dec.) after crystallization from isopropyl alcohol. Anal. Calcd. for C$_{20}$H$_{26}$ClNO$_6$; C, 58.23; H, 6.36. Found: C, 58.32; H, 6.41.

EXAMPLE 67

4-(3'-Chlorophenyl)-α,α,1-trimethyl-4-piperidinemethanol Acetate (I, m=2; $R^1, R^5R^6$=Me; $R^2, R^3$=H; $R^4$=3-ClC$_6$H$_4$; $R^7$=CH$_3$CO)

A mixture of 1.04 g of 4-(3'-Chlorophenyl)-α,α-1-trimethyl-4-piperidinemethanol (Example 2) and 10 mL of acetic anhydride was heated under reflux for 2 hours. Removal of the excess acetic anhydride followed by short-path distillation of the residue (170° bath temperature, 1 micron) gave 1.07 g of the title compound as an oil that slowly crystallized. NMR (CDCl$_3$): δ7.3 (s,1H); 7.2 (m,3H); 2.7 (d,2H); 2.2 (s,3H), 2.0 (s,3H); 1.8-2.5 (m,6H) and 1.4 (s,6H). High-resolution mass spectrum m/e calcd. for C$_{17}$H$_{24}$ClNO$_2$; 309.1495; measured: 309.1486.

EXAMPLE 68

4-(3'-Chlorophenyl)-4-(1'''-methoxymethyl)-1-methyl-piperidine (I, m=2; $R^1, R^5, R^7$=Me; $R^2, R^3, R^6$=H; $R^4$=3-ClC$_6$H$_4$)

Potassium hydride oil suspension (3.80 g of 35%; 33 mmoles) was washed with hexane, 15 mL of tetrahydrofuran was added, and the suspension was treated with 4.25 g (16 mmoles) of 4-(3'-chlorophenyl)-α,1-dimethyl-4-piperidinemethanol (Example 1) dissolved in 15 mL of tetrahydrofuran. The mixture was stirred at room temperature for 1 hour; methyl iodide (9.1 g, 64 mmoles) was added which caused the temperature to rise to 50°. Methanol (5 mL) was added after stirring for 2.75 hours, keeping the temperature below 25°. Water and chloroform were added, and the mixture was filtered to remove 4.70 g of the methiodide of the title compound. This solid was combined with the products obtained on removal of the solvent from the chloroform layer, and heated with 7.0 g of potassium methylmercaptide in 30 mL of dimethyl formamide in an 80° oil bath for 2.5 hours. The solvent was removed, water was added to the residue and the mixture was extracted with methylene chloride. Removal of the solvent from the dried extracts and short-path distillation of the residue (130° bath temperature, 1 micron) gave 3.94 g (88% yield) of the title compound as an oil. NMR (CDCl$_3$): δ7.2-7.4 (m,4H); 3.3 (s,3H); 3.2 (quartet, J=7 Hz,1H); 2.7 (m,2H); 2.2 (s,3H); 1.8-2.4 (m,6H); and 0.9 (d,J=7 Hz,3H). High resolution mass spectrum: m/e calcd. for C$_{15}$H$_{22}$ClNO: 267.1390; measured: 267.1393.

EXAMPLE 69

4-(3'-Chlorophenyl)-4-(1'''-benzyloxymethyl)-1-methyl-piperidine (I, m=2; $R^1, R^5$=Me; $R^2, R^3, R^6$=H; $R^4$=3-ClC$_6$H$_4$; $R^7$=C$_6$H$_5$CH$_2$)

Following the procedure of Example 53, but using benzyl bromide in place of methyl iodide, the title compound was obtained as an oil, distilling at a bath temperature of up to 210° at 1 micron. NMR (CDCl$_3$): δ7.2-7.4 (m,9H); 3.4 (quartet, J=7 Hz,1H); 2.7 (m,2H); 2.4 (m,1H); 2.2 (s,3H); 2.0 (m,5H) and 0.9 (d,J=7 Hz,3H). High resolution mass spectrum: calcd. for C$_{21}$H$_{26}$ClNO: m/e 343.1703; measured: 343.1693.

EXAMPLE 70

3-(3'-Chlorophenyl)-α,α,1-trimethyl-3-pyrrolidinemethanol (I, m=1; $R^1R^5R^6$=Me; $R^2, R^3, R^7$=H; $R^4$=3-ClC$_6$H$_4$)

A solution of 2.83 g of ethyl 3-(3'-chlorophenyl)-1-methyl-3-pyrrolidinecarboxylate in 5 mL of tetrahydrofuran was added to 8 mL of 3M methylmagnesium chloride in tetrahydrofuran and the mixture was heated under reflux for 4 hours. Ten percent hydrochloric acid was added and the mixture was washed with ether. The aqueous phase was made basic with ammonium hydroxide solution and extracted with methylene chloride. Removal of the solvent from the dried extract gave 1.94 g of crude title compound. It was purified by chromatography on silica (elution with 3:1 methylene chloride/methanol), followed by crystallization from acetonitrile m.p. 98°-99°. NMR (CDCl$_3$): δ7.0-7.3 (m,4H); 3.7 (d, J=7 Hz,1H); 3.2 (m,2H); 2.8 (m,1H); 2.4 (d, J=10 Hz,1H); 2.4 (s,3H) 2.2 (m,2H); 1.2 (s,3H) and 1.1 (s,3H). High resolution mass spectrum: m/e calcd. for C$_{14}$H$_{20}$ClNO: 253.1233; measured: 253.1235.

The starting material, ethyl 3-(3'-chlorophenyl)-1-methyl-3-pyrrolidine carboxylate, was prepared from 3-chlorobenzyl cyanide by the procedure of R. L. Jacoby, K. A. Nieforth, and R. E. Willete, *J. Med. Chem.*, 17,453 (1974). NMR (CDCl$_3$): δ7.1-7.4 (m,4H); 4.1 (quartet, J=7 Hz,2H); 3,6 (d, J=8 Hz,1H); 2.9 (m,2H); 2.7 (d, J=8 Hz, 1H); 2.0-2.5 (m+s,5H) and 1.2 (t,J=7 Hz,3H).

EXAMPLE 71

4-(3'-Chlorophenyl)-α,1-dimethyl-2,3,4,5,6,7-hexahydro-1H-azepine-4-methanol (I, m=3; $R^1, R^5$=Me; $R^4$=3-ClC$_6$H$_4$; $R^2, R^3, R^6, R^7$=H)

Sodium borohydride (0.22 g) was added with cooling to a solution of 1.0 g of 1-[4-(3-chlorophenyl)-1-methyl-4-(2,3,4,5,6,7-hexahydro-1H-azepinyl]ethanone in 2 mL of ethanol. The mixture was stirred at room temperature for 18 hours. Water was added and the mixture was extracted repeatedly with methylene chloride. Removal of the solvent and crystallization of the residue from aceto-nitrile gave 0.54 g of the title compound, m.p. 123°-124° NMR (CDCl$_3$): δ7.2-7.4 (m,4H); 3.6 (quartet, J=7 Hz,1H); 2.7 (m,2H); 2.4 (m,1H); 2.2 (s,3H); 1.6-2.0 (m,8H) and 1.0 (d, J=7 Hz,3H). High-resolution mass spectrum: m/e calcd. for C$_{15}$H$_{22}$ClNO: 267.1390; measured: 267.1388.

The starting material, 1-[4-(3-chlorophenyl)-1-methyl-4-(2,3,4,5,6,7-hexahydro-1H-azepinyl]ethanone was prepared as described in Example 1 by the addition of methylmagnesium chloride to 4-(3'-Chlorophenyl-α,1-dimethyl-2,3,4,5,6,7-hexahydro-1H-azepine-4-carbonitrile. The latter was prepared from 3-chlorobenzyl cyanide by the procedure of J. Diamond, W. F. Bruce and F. T. Tyson, *J. Org. Chem.*, 399 (1957).

TABLE 2

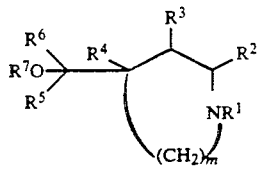

| Ex. No. | $R^1$ | $R^2$ | $R^3$ | $R^4$ | $R^5$ | $R^6$ | $R^7$ | m | Mp °C. |
|---|---|---|---|---|---|---|---|---|---|
| 66 | Me | H | H | 3-ClC$_6$H$_4$ | Me | H | Ac | 2 | 194 (dec)** |
| 67 | Me | H | H | 3-ClC$_6$H$_4$ | Me | Me | Ac | 2 | (solid)* |
| 68 | Me | H | H | 3-ClC$_6$H$_4$ | Me | H | Me | 2 | (oil)* |
| 69 | Me | H | H | 3-ClC$_6$H$_4$ | Me | H | CH$_2$C$_6$H$_5$ | 2 | (oil)* |
| 70 | Me | H | H | 3-ClC$_6$H$_4$ | Me | Me | H | 1 | 98–99 |
| 71 | Me | H | H | 3-ClC$_6$H$_4$ | Me | H | H | 3 | 123–124 |
| 72 | Me | H | H | 3-ClC$_6$H$_4$ | Me | Me | H | 3 | |
| 73 | Me | H | H | 3-ClC$_6$H$_4$ | Me | H | H | 1 | |
| 74 | Me | H | H | 3-CF$_3$C$_6$H$_4$ | Me | Me | H | 3 | |
| 75 | Me | H | H | 3-CF$_3$C$_6$H$_4$ | Me | Me | H | 1 | |
| 76 | Me | H | H | 3-ClC$_6$H$_4$ | Me | Me | Me | 1 | |
| 77 | Et | Me | H | 3-thienyl | Me | Me | H | 3 | |
| 78 | n-Pr | H | Me | 2-bromothienyl | Me | Et | H | 3 | |
| 79 | Me | H | H | 3-BrC$_6$H$_4$ | Me | Me | H | 1 | |
| 80 | Me | H | H | 3-BrC$_6$H$_4$ | Me | Me | H | 3 | |
| 81 | Me | H | H | 3-ClC$_6$H$_4$ | Me | H | Ac | 3 | |
| 82 | Me | H | H | 2-thienyl | Me | H | H | 1 | |
| 83 | Me | H | H | 2-thienyl | Me | Me | H | 3 | |
| 84 | Me | H | H | 3-ClC$_6$H$_4$ | Me | H | n-butyl | 2 | |
| 85 | Me | H | H | 3-ClC$_6$H$_4$ | Me | Me | COn-butyl | 2 | |

*For NMR and HRMS data see experimental procedure
**Fumarate salt

DOSAGE FORMS

The analgesic agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. Usually, a daily dosage of active ingredient can be about 0.001 to 50 milligrams per kilogram of body weight. Ordinarily, a total of 0.01 to 20, preferably 0.1 to 10, milligrams per day per kilogram of body weight, given in divided doses 2 to 4 times a day or in sustained release form, is effective to obtain the desired therapeutic results.

Dosage forms (compositions) suitable for internal administration can contain about 0.25 to about 400 milligrams of active ingredient per unit. In such pharmaceutical compositions the active ingredient will ordinarily be present in a mount of about 0.01–90% by weight, based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms, or rectally in the form of suppositories.

Gelatin capsules can contain the active ingredient and powdered carriers, such as lactose, sucrose, mannitol, starch, cellulose derivatives, magnesium stearate and stearic acid. Similar diluents can be used to make compressed tablets. Both tablets and capsules can be manufactured as sustained release of medication over a period of hours. Compressed tablets can be sugar coated or film coated to mask any unpleasant taste and protect the tablet from the atmosphere, or they can be enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols, such as propylene glycol or the polyethylene glycols, are suitable carriers for parenteral solutions. Solutions for parenteral administration contain preferably a water-soluble salt of the active ingredient, suitable stabilizing agents, such as sodium bisulfite, sodium sulfite and ascorbic acid, either alone or combined, are suitable stabilizing agents. Also used are citric acid and its salts and sodium EDTA (ethylenediaminetetraacetic acid). In addition, parenteral solutions can contain preservatives, such as benzalkonium chloride, methyl- or propylparaben and chlorobutanol.

Suppositories can contain the active ingredient in a suitable oleaginous or water-soluble base. The oleaginous class includes cocoa butter and other fats with similar properties; the water-soluble class includes the polyethylene glycols.

Suitable pharmaceutical carriers are described by E. W. Martin in *Remington's Pharmaceutical Sciences*, a standard reference text in this field.

Useful pharmaceutical dosage forms for administration of the compounds of this invention are illustrated below.

CAPSULES (Hard)

Hard capsules can be prepared by filling standard two-piece hard gelatin capsules with the following mixture using conventional encapsulating equipment:
  Active ingredient: 1 mg
  Lactose: 125 mg
  Talc: 12 mg
  Magnesium stearate: 3 mg.

CAPSULES (Soft)

A mixture of active ingredient in soybean oil can be prepared and injected by means of a positive displacement pump in gelatin to form soft gelatin capsules containing 5 mg of the active ingredient. The capsules can be washed in petroleum ether and dried.

TABLETS

Tablets can be prepared by conventional procedures so that each unit will contain:
  Active ingredient: 1 mg
  Spray dried lactose: 150 mg
  Microcrystalline cellulose: 35 mg
  Magnesium stearate: 3 mg.

PARENTERAL

Parenteral composition suitable for intramuscular administration can be prepared so that each mL contains, percentages being by weight:
  Active ingredient: 1 mg
  Sodium carboxymethyl cellulose: 0.75%
  Polysorbate 80: 0.04%
  Benzyl alcohol: 0.9%
  Sodium chloride: 0.9%
  Water for injection Q.S.: 1 mL.

SUSPENSION

An aqueous suspension can be prepared for oral administration so that each 5 mL contain, percentages being by weight:
  Active ingredient: 5 mg
  Methylcellulose: 5%
  Carboxymethyl cellulose: 5%
  Syrup: 30%
  Polysorbate 80: 0.2%
  Sodium saccharin: 2 mg
  Cherry flavor: 0.1%
  Sodium benzoate: 5 mg
  Water Q.S.: 5 mL.

MOUSE ANTIPHENYLQUINONE WRITHING (PQW) TEST

The anti-phenylquinone writhing (PQW) test modified from the methods of Siegmund et al. (Proc. Soc. Exp. Biol. Med. 95: 729–731, 1957) and Blumberg et al. (Proc. Exp. Biol. Med. 118: 763–767, 1965) was used to assess analgesia in mice. Male CF1 mice (Charles River Breeding Laboratories, Wilmington, Mass.), fasted for 16–22 hr and weighing 18–23 g, were injected with randomized and coded doses of test compounds, then challenged with 1.25 mg/kg i.p. phenyl-p-benzoquinone (phenylquinone) 5 min prior to the specified observation time. The phenylquinone solution (0.1 mg/ml in 5% aqueous ethanol) was prepared daily and stored in foil-wrapped amber bottles to limit degradation. Mice were observed 10 min for the presence or absence of the characteristic abdominal constriction and stretching response beginning 30 min after injection of the test compound. Analgetic activity was calculated as the percentage of mice failing to respond to the phenylquinone challenge dose. Greater than 95% of the control (vehicle-treated) mice exhibited a writhing response. Median effective doses (ED50's) and 95% confidence limits were determined numerically by the methods of Thompson (Bacteriological Rev. 11: 115–145, 1947), and Litchfield and Wilcoxon (J. Pharmacol. Exp. Ther. 96: 99–113, 1949).

The data shown in Table 3 show the PQW $ED_{50}$ values for the compounds of the aforesaid examples.

TABLE 3

| Ex. No. | Mouse PQW $ED_{50}$ (mg/kg) S.C. | P.O. | |
|---|---|---|---|
| 1 | 8.1 | 19.0 | |
| 1a | 16.1 | 10.0 | |
| 2 | 62.0 | >81.0 | |
| 3 | 19.0 | 38.0 | |
| 4 | >81.0 | >81.0 | Inactive |
| 5 | 24.0 | >81.0 | |
| 6 | 54.0 | >81.0 | |
| 7 | 38.0 | >81.0 | |
| 8 | 30.0 | >81.0 | |
| 9 | >81.0 | 32.0 | |
| 10 | 6.5 | 16.0 | |
| 11 | >81.0 | >81.0 | Inactive |
| 12 | >81.0 | >81.0 | Inactive |
| 13 | 4.7 | 47.0 | |
| 14 | 54.0 | >81.0 | |
| 15 | 19.0 | 30.0 | |
| 16 | >81.0 | >81.0 | Inactive |
| 17 | >81.0 | >81.0 | Inactive |
| 25 | 16.0 | >81.0 | |
| 26 | 13.0 | 19.0 | |
| 27 | 13.0 | 16.0 | |
| 29 | 6.8 | 47.0 | |
| 34 | 38.0 | >81.0 | |
| 35 | 16.0 | 30.0 | |
| 36 | 67.0 | >81.0 | |
| 37 | 48.0 | >81.0 | |
| 41 | 19.0 | 24.0 | |
| 42 | 27.0 | 54.0 | |
| 43 | 13.0 | 36.0 | |
| 44 | 6.5 | 24.0 | |
| 45 | 4.2 | 54.0 | |
| 46 | >81.0 | >81.0 | Inactive |
| 50 | 24.0 | 67.0 | |
| 66 | 13.0 | 19.0 | |
| 67 | 1.8 | 5.2 | |
| 68 | 6.5 | 19.0 | |
| 69 | 62.0 | >81.0 | |
| 70 | 10.0 | 13.0 | |
| 71 | 8.1 | 16.0 | |

Table 4 illustrates that the 3° carbinols within the scope of U.S. Pat. No. 4,485,109 have utility as analgesic agents.

TABLE 4

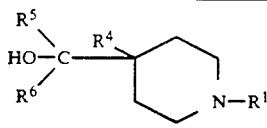

| Ex. No. | $R^1$ | $R^4$ | $R^5$ | $R^6$ | S.C. | P.O. |
|---|---|---|---|---|---|---|
| A | Me | 3-ClC$_6$H$_4$ | Me | Me | 10.0 | 16.0 |
| B | Me | 3-ClC$_6$H$_4$ | Me* | Me | 16.0 | 10.0 |
| C | Me | 2-FC$_6$H$_4$ | Me | Me | 38.0 | >81.0 |
| D | Me | 3,4-F$_2$C$_6$H$_3$ | Me | Me | >81.0 | >81.0 Inactive |
| E | Me | 3-ClC$_6$H$_4$ | Me | Et | 16.0 | 47.0 |
| F | Me | 3-ClC$_6$H$_4$ | Me | n-Pr | | |
| G | Me | 3-ClC$_6$H$_4$ | Me | n-Bu | 24.0 | 67.0 |
| H | Me | 3-ClC$_6$H$_4$ | —(CH$_2$)$_4$— | | 13.0 | 16.0 |
| I | Me | 3-ClC$_6$H$_4$ | —(CH$_2$)$_5$— | | 47.0 | >81.0 |
| J | Me | 3,5-Cl$_2$C$_6$H$_3$ | Me | Me | 16.0 | 16.0 |
| K | Et | 3-ClC$_6$H$_4$ | Me | Me | 47.0 | >81.0 |
| L | n-Pr | 3-ClC$_6$H$_4$ | Me | Me | 49.0 | >81.0 |
| M | Me | 4-Me$_2$NC$_6$H$_4$ | Me | Me | NT | <108.0 |
| N | Me | 3-CF$_3$C$_6$H$_4$ | Me | Me | 19.0 | 47.0 |
| O | Me | C$_6$H$_5$ | Me | Me | 18.0 | 47.0 |
| P | Me | 3-FC$_6$H$_4$ | Me | Me | 10.0 | >81.0 |
| Q | Me | 4-FC$_6$H$_4$ | Me | Me | 27.0 | 12.0 |
| R | Me | 3-ClC$_6$H$_4$ | Et | Et | 8.1 | 38.0 |
| S | Me | 2-MeC$_6$H$_4$ | Me | Me | 6.8 | 23.0 |
| T | Me | 3-MeC$_6$H$_4$ | Me | Me | NT | 78.0 |
| U | Me | 3,5-Me$_2$C$_6$H$_3$ | Me | Me | 4.5 | 47.0 |
| V | Me | 3-CF$_3$C$_6$H$_4$ | Me | Et | NT | 23.0 |
| W | Me | 3-CF$_3$C$_6$H$_4$ | —(CH$_2$)$_4$— | | 16.0 | 12.0 |
| X | Me | 3-FC$_6$H$_4$ | Me | Me | 10.0 | >81.0 |
| Y | Me | 3-CF$_3$C$_6$H$_4$ | —(CH$_2$CHMeCH$_2$CH$_2$)— | | NT | 25.0 |
| AA | Me | 3-HOC$_6$H$_4$ | Me | Me | 62.0 | >81.0 |
| BB | Me | 3-MeOC$_6$H$_4$ | Me | Me | 12.0 | 19.0 |
| CC | Me | 3-MeOC$_6$H$_4$ | Me | Et | 23.0 | 68.0 |
| DD | Me | 3-MeOC$_6$H$_4$ | Et | Et | NT | 12.0 |
| EE | Me | 3-MeOC$_6$H$_4$ | —(CH$_2$)$_3$— | | 22.0 | >54.0 |
| FF | Me | 3-MeOC$_6$H$_4$ | —(CH$_2$)$_4$— | | 16.0 | 47.0 |
| GG | Me | 3-MeOC$_6$H$_4$ | —(CH$_2$)$_5$— | | NT | <108.0 |
| HH | Me | 3-EtOC$_6$H$_4$ | Me | Me | 9.0 | 32.0 |
| II | Me | 4-MeSC$_6$H$_4$ | Me | Me | NT | 59.0 |
| JJ | Me | 3-Phenyl | Me | Me | NT | 89.0 |
| KK | Me | 4-Phenyl | Me | Me | NT | 37.0 |
| LL | Me | 4-PhO | Me | Me | 68.0 | >81.0 |
| MM | Me | 2-Naphthyl | Me | Me | 27.0 | 47.0 |
| | Me | 5-Me-2-thienyl | Me | Me | 9.0 | 36.0 |

*hydrochloride

PROTOCOL FOR DETECTING ANTIDEPRESSANT ACTIVITY

The prevention of tetrabenazine-induced sedation and depression in mice is a standard procedure used to detect and compare antidepressant compounds. The activity of antidepressant compounds in this procedure correlates well with human efficacy. (Barnett, et al., Int. J. Neuropharmac. 8: 73-79, 1969, and Vernier, et al., "The Pharmacodynamics of Amitriptyline" in *Psychosomatic Medicine* (Nodine & Moyer, editors) pp. 683-690, 1962).

Male CF mice (Charles River Breeding Laboratories, Wilmington, Mass.), fasted for 16-22 hours and weighing 18-25 g, were injected with randomized and coded does of test compounds, then challenged with 52 mg/kg i.p. tetrabenazine methane sulfonate 30 minutes prior to the specified observation time. The tetrabenazine methane sulfonate solution (5.2 mg/ml in distilled water) was prepared daily and stored in foil-wrapped amber bottles to limit degradation. Mice were observed for the presence or absence of the characteristic ptosis (eyelid closure) and exploratory loss induced by tetrabenazine. Exploratory loss was defined as failing to move to the perimeter of a 5 inch (12.7 cm) circle within 15 seconds of being placed at the center of the circle. Ptosis was defined as both eyelids closed 50% or more compared to normal. Antidepressant activity was calculated as the percentage of mice failing to respond to the tetrabenazine challenge dose. Greater than 95% of the control (vehicle-treated) mice exhibited exploratory loss and ptosis. Median effective does (ED$_{50}$'s) were estimated using the Moving Average method of Thompson (Bacteriological Rev. 11: 115-145, 1947).

The data in Table 5 show ED$_{50}$ values for the compounds of the aforesaid examples.

TABLE 5

Antagonism of Tetrabenazine-Induced Depression in Mice Orally at One Hour Post-Drug

| Example | Exploratory Loss | Oral Ed$_{50}$ (mg/kg) for Prevention of Ptosis |
|---|---|---|
| 1 | 0.92 | 0.74 |
| 12 | NT | 1.03 |
| 16 | NT | 28.00 |
| 17 | NT | 1.30 |

PROTOCOL FOR ANOREXIA DATA FROM CNS SCREEN

Male mice weighing 18-25 grams and fasted overnight for 17-21 h were used in these studies. At 0.5 h after administration of graded oral doses of compound prepared in aqueous Methocel ® (methylcellulose, viscosity 100 CPS, grade A15C, Dow Chemical Co.) and dosed at 0.1 mL per 10 grams of body weight, each mouse was transferred to an individual, clear, Lucite ® compartment (13.3 cm × 12.7 cm × 12.7 cm) with a wire mesh floor having 0.64 cm × 0.64 cm openings. Five compartments were linearly arranged in each cage unit. Inside each compartment was a section of a black Lucite ® bar (13 cm × 1.2 cm × 1.2 cm), in the top of which were ten spot depressions (0.8 cm diameter), each containing 0.05 mL of 50% sweetened condensed milk. Ten (10) minutes later the mice were removed from to the compartments and the number of milk spots consumed by each mouse was counted. Fractions of spots consumed were also estimated and counted. Data were expressed as % decrease from control. $ED_{50}$ values were estimated using linear regression analysis.

The data tabulated in Table 6 show that certain compounds of this invention have utility as anorectic agents, and thus may be useful in treating obesity.

TABLE 6

| Example | $ED_{50}$ for Anorexia (mg/kg) |
|---------|--------------------------------|
| 1       | 20                             |
| 16      | 22                             |

What is claimed is:

1. A method of treating pain in a mammal which comprises administering to said mammal an analgesic effective amount of a compound of the formula:

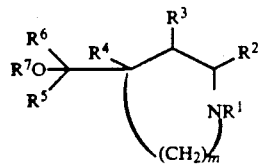

wherein
m is 2;
$R^1$ is $CH_3$, $C_2H_5$, $n$-$C_3H_7$, or allyl;
$R^2$ and $R^3$ independently are H or alkyl of 1-4 carbon atoms; or $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;
$R^4$ is:
(a) phenyl or

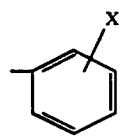

where X is one or two substituents, the same or different, selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl or 2-, 3-, or 4-biphenyl where either or both aromatic groups are substituted with 1 or 2 substituents, the same or different, selected from F, Cl, alkyl, perfluoroalkyl, alkoxy, aryloxy, alkylthio, perfluoroalkoxy, arylthio, perfluoroalkylthio and dialkylamino, said alkyl and alkoxy groups being of 1-12 carbon atoms and said aryl groups being of 6-12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1-4 carbon atoms;

(e) 2- or 3-thienyl optionally substituted with one substituent selected from Cl, Br, or alkyl of 1-4 carbon atoms; or (f) 2- or 3-benzothienyl or benzofuryl optionally substituted on the aromatic ring with Cl, Br, or $CF_3$;

$R^5$ is alkyl of 1-4 carbon atoms, or is taken together with $R^6$ to form a branched or unbranched alkylene bridge of 3-11 carbon atoms;

$R^6$ is H, alkyl of 1-4 carbon atoms, or is taken together with $R^5$ to form a branched or unbranched alkylene bridge of 3-11 carbon atoms; and $R^7$ is H, alkyl of 1-4 carbon atoms, alkanoyl of 1-4 carbon atoms, or —$CH_2$ phenyl; or a pharmaceutically salt or N-oxide thereof, provided that when 1) $R^1$, $R^5$ and $R^6$ are methyl, and $R^2$ and $R^3$ are H, then $R^4$ is not $3,4$-$F_2C_6H_3$, $3,4$-$Cl_2C_6H_3$, p-t-butylphenyl, $2,3$-$(MeO)C_6H_3$, $2,5$-$(MeO)_2C_6H_3$, or 3-pyridyl;

2) $R^1$ is methyl and $R^5$ and $R^6$ are taken together as —$(CH_2)_7$, then $R^4$ is not $3$-$MeOC_6H_4$; and 3) $R^1$ and $R^5$ are methyl, and $R^2$, $R^3$ and $R^6$ are H, then $R^4$ is not $2$-$FC_6H_4$, $4$-$BrC_6H_4$, $2$-$CH_3C_6H_4$, $4$-$CH_3OC_6H_4$, or $4$-$CF_3C_6H_4$.

2. A method of treating pain in a mammal which comprises administering to said mammal an analgesic effective amount of a compound of Formula (I) of claim 1 wherein $R^1$ is $CH_3$.

3. A method of treating pain in a mammal which comprises administering to said mammal an analgesic effective amount of a compound of Formula (I) of claim 1 wherein $R^2$ and $R^3$ are both H.

4. A method of treating pain in a mammal which comprises administering to said mammal an analgesic effective amount of a compound of Formula (I) of claim 1 wherein $R^4$ is $C_6H_4X$ wherein X is Cl, Br, F, or $CF_3$; or $R^4$ is 2- or 3- thienyl.

5. A method of treating pain in a mammal which comprises administering to said mammal an analgesic effective amount of a compound of Formula (I) of claim 1 wherein $R^5$ is $CH_3$.

6. A method of treating pain in a mammal which comprises administering to said mammal an analgesic effective amount of a compound of Formula (I) of claim 1 wherein $R^6$ is H or $CH_3$.

7. A method of treating pain in a mammal which comprises administering to said mammal an analgesic effective amount of a compound of Formula (I) of claim 1 wherein $R^7$ is H.

8. A method of treating pain in a mammal which comprises administering to said mammal an analgesic effective amount of a compound of Formula (I) of claim 1 wherein m is 2.

9. A method of treating pain in a mammal which comprises administering to said mammal an analgesic effective amount of a compound of Formula (I) of claim 1 wherein m is 2, $R^1$ and $R^5$ are $CH_3$; $R^2$, $R^3$, $R^6$, and $R^7$ are H; and $R^4$ is 2- or 3-thienyl, or $C_6H_4X$ where X is Cl, Br, F, or $CH_3$.

10. A method of treating pain in a mammal which comprises administering to said mammal an analgesic effective amount of a compound of Formula (I) of claim 1 wherein said compound is 4-(3-thienyl)-α,α,1,-trimethyl-4-piperidinemethanol, or a pharmaceutically suitable salt thereof.

11. A method of treating pain in a mammal which comprises administering to said mammal an analgesic effective amount of a compound of Formula (I) of claim 1 wherein said compound is 4-(3'-chlorophenyl)-α,1-dimethylpiperidinemethanol, or a pharmaceutically suitable salt thereof.

12. A method of treating pain in a mammal which comprises administering to said mammal an analgesic effective amount of a compound of Formula (I) of claim 1 wherein said compound is 4-(3'-bromophenyl)-α,1-dimethylpiperidinemethanol, or a pharmaceutically suitable salt thereof.

13. A method of treating pain in a mammal which comprises administering to said mammal an analgesic effective amount of a compound of Formula (I) of claim 1 wherein said compound is 4-(3'-bromophenyl)-α,α,1-trimethyl-4-piperidinemethanol, or a pharmaceutically suitable salt thereof.

14. A method of treating pain in a mammal which comprises administering to said mammal an analgesic effective amount of a compound of Formula (I) of claim 1 wherein said compound is 4-(2-thienyl)-α,1-dimethyl-piperidinemethanol, or a pharmaceutically suitable salt thereof.

15. A method of treating pain in a mammal which comprises administering to said mammal an analgesic effective amount of a compound of Formula (I) of claim 1 wherein said compound is 4-(3-thienyl)-α,1-dimethyl-piperidinemethanol, or a pharmaceutically suitable salt thereof.

16. A method of treating pain in a mammal which comprises administering to said mammal an analgesic effective amount of a compound of Formula (I) of claim 1 wherein said compound is 4-(4'-trifluoromethyl-phenyl)-α,1-dimethylpiperidinemethanol, or a pharmaceutically suitable salt thereof.

* * * * *